United States Patent [19]

Hofmann

[11] Patent Number: Plant 7,083

[45] Date of Patent: Dec. 26, 1989

[54] DISTINCT VARIETY OF GERANIUM PLANT NAMED FOX

[75] Inventor: Christa Hofmann, Dresden, German Democratic Rep.

[73] Assignee: Oglevee Ltd., Connellsville, Pa.

[21] Appl. No.: 298,341

[22] Filed: Jan. 18, 1989

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new geranium cultivar is distinguished by its brilliant fluorescent fuschia color with orange highlights. It is a compact, upright, well-branched plant of excellent conformation. The attractive dark foliage compliments the brilliant color of the flower and the healthy foliage is an improvement to current varieties in this color class.

1 Drawing Sheet

BACKGROUND OF THE NEW PLANT

The present invention comprises a new and distinct cultivar of *Pelargonium hortorum* which is a zonal geranium known by the varital name Fox. The new variety is a seedling resulting from a cross of the varieties Kardinal and Purpurball (commercialized in the United States as Veronica under U.S. Plant Pat. No. 5,054).

The new variety was discovered in a selective breeding program by Mrs. Christa Hofmann.

The new cultivar was discovered in 1984 at the VEB Saatzucht Zierpflanzen Dresden, German Democratic Republic, and was first asexually reproduced by cuttings in Dresden, German Democratic Republic, and has been repeatedly asexually reproduced over a two-year period by cuttings for Oglevee Associates, Inc. in Connellsville, Pa. It has also been trialed and field tested over the summers of 1987 and 1988 in Connellsville, Pa. and has been found to retain its distinctive characteristics through successive propogations.

The new cultivar is a compact, upright well-branched plant of excellent conformation and has attractive dark foliage which compliments the brilliant fluorescent fuschia color of the flower. The healthy foliage is an improvement to the current varieites such as Aurora in this color class. The plant is slightly larger than Veronica and the overall color contains more purple tones than Veronica.

The new cultivar, when grown in a greenhouse in Connellsville, Pa., using natural light and 60° F. night temperature, 68° F. day temperature and 71° F. vent temperature, has a response of eight weeks from a well-rooted cutting to a flowering plant in a four inch (10 cm) pot.

DESCRIPTION OF THE DRAWING

The accompanying photographic drawing illustrates a new cultivar, the color being as nearly true as possible with color illustrations of this type.

DESCRIPTION OF THE NEW PLANT

The following detailed description set forth the characteristics of the new cultivar. The data which defines these characteristics were collected from asexual reproductions carried out for Oglevee Associates, Inc., in Connellsville, Pa. The plant history was taken on eight-week plants in which rooted cuttings were potted Aug. 4, 1987 and subsequently flowered on Sept. 20, 1987.

Plants were grown in a soilless media with constant fertilizer of 250–275 parts per million nitrogen and potassium. Readings were taken with 200–220 candles of fluorescent cool, white light. Color references are primarily to the R.H.S. Colour Chart of The Royal Horticultural Society of London.

THE PLANT

Classification:

*Botanical.*—*Pelargonium* × *hortorum.*

*Commercial.*—Zonal Florists' Geranium.

Form: Bush. Basal branching, free and early flowering, upright habit.

Height: 23.0–26.0 cm from media surface.

Growth: Free-branching from base, medium internode length.

Strength: Stands upright without artificial support.

Foliage: Large leaves with zonation of darker green than leaf; not easily noticed.

Leaves: Leaf description of a mature, fully expanded leaf at least 4 nodes below apical meristem.

*Size.*—8.0–15.0 cm.

*Shape.*—Reniform, cordate base.

*Margin.*—Crenate.

*Texture.*—Downy, dull (not reflective).

*Color.*—Outside margin — Green group 137A.

*Center.*—Green group 137B.

*Ribs and veins.*—Palmate veination; Yellow-green group 144B

Petioles: Stalked petiole; 7.0–10.0 cm; Green group 137B to Green group 144A.

Stem:

*Color.*—Yellow-green group 144A.

*Internodes.*—1.5–3.0 cm.

THE BUD

The umbel contains 20–35 flower buds.

As the petals emerge from the sepals, they appear Red-purple group 64B.

INFLORESCENCE

Blooming habit: Continuous, upright, semi-double, hemispherical in shape.

Size: 8.0–12.0 cm across.

Borne: Umbel, florets on pedicel, pedicel on peduncle; 4.0–6.0 cm above foliage.

Tonality from a distance: Fluorescent fuschia with orange highlights on top of medium green foliage.

Florets:

*Form.*—Flat with petiloids.

*Color.*—Top — Red-purple group 66A. Bottom — Red-purple group 61C.

*Petals.*—7–10 separate-not united; margin entire obovate; palmate veination; smooth; flat to slightly cupped.

Size.—5.0 cm.

*Texture.*—Smooth surface.

Petaloids:

*Quantity.*—7 to 10.

*Shape.*—There are two types of petaloid shapes. The center petaloids are narrow, elongated and twisted. The outside petaloids are petal-like in shape.

*Color.*—Orange-red group 33A base of the center of the petaloids. The larger petal-like petaloids are Red-purple group 57B.

Medicel:

*Length.*—3.0–4.0 cm in length.

*Color.*—Apical end — Red-purple group 59B; basal end — Yellow-green group 144B.

Peduncle: Arises from node; opposite leaf petiole.

REPRODUCTIVE ORGANS

Stamens:

*Anthers.*—Eliptical 1.0–2.0 mm.

*Filaments.*—White at base — colored toward tip same as center of florets; irregular in shape; flat at base and twisted at tip; 5.0–7.0 mm in length.

*Pollen.*—Golden brown initially; later turns dark brown.

Pistils:

*Number.*—1 to 5 parted stigma.

*Length.*—0.5–0.9 cm in length.

*Stigma.*—5 parted; colored same as floret.

Style.—1; pale red to reddish color; 2.0–3.0 mm in length.

Ovaries: 3.0–5.0 mm in length; yellow-green; very pubescent; superior.

Fruit: None observed.

I claim:

1. A new and distinct variety of geranium plant characterized by a compact, upright branched plant of excellent conformation, dark foliage which compliments the brilliant two-tone effect of the florets, a healthy foliage and a brilliant fluorescent fuschia color substantially as herein shown and described.

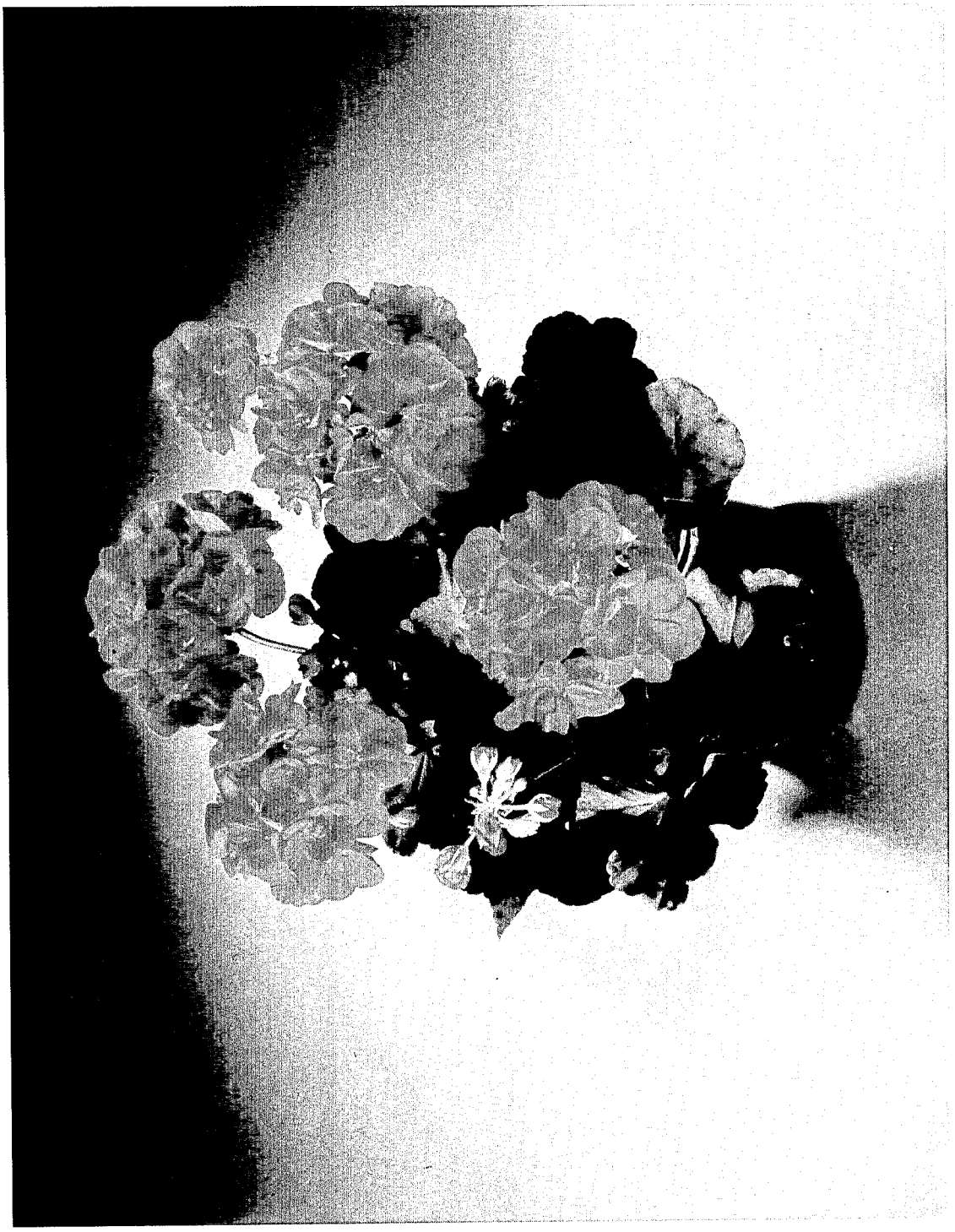

* * * * *